United States Patent [19]

Benningfield, Jr.

[11] 4,009,998
[45] Mar. 1, 1977

[54] ACID CONCENTRATION MEASUREMENT

[75] Inventor: L. V. Benningfield, Jr., Bartlesville, Okla.

[73] Assignee: Phillips Petroleum Company, Bartlesville, Okla.

[22] Filed: Sept. 5, 1975

[21] Appl. No.: 610,800

[52] U.S. Cl. .............................................. 23/230 R
[51] Int. Cl.² ....................................... G01N 27/06
[58] Field of Search ..................... 23/230 R, 253 R; 261/94

[56] References Cited
UNITED STATES PATENTS

| 2,559,090 | 7/1951 | Potter | 23/253 R X |
| 2,977,199 | 3/1961 | Quittner | 23/230 R |
| 3,466,228 | 9/1969 | Trebes | 23/230 R X |
| 3,468,637 | 9/1969 | Hammond | 261/94 X |
| 3,531,252 | 9/1970 | Rivers et al. | 23/230 R |
| 3,904,365 | 9/1975 | Larson et al. | 23/230 R |
| R22,696 | 11/1945 | Frischer | 261/94 |

Primary Examiner—Robert M. Reese

[57] ABSTRACT

The acid concentration of a test material is measured by passing a stream of water through a mixing device at a predetermined rate, adding a predetermined volume of the test material to the water upstream of the mixing device, and measuring the electrical conductivity of the mixed effluent stream from the mixing device.

6 Claims, 3 Drawing Figures

ACID CONCENTRATION MEASUREMENT

It is often desirable to measure the concentration of acid in a fluid stream. For example, hydrofluoric acid and sulfuric acid are employed as catalysts in the alkylation of olefins with isoparaffins. The recycle acid stream fed to the reactor in an HF alkylation process may have a concentration of the order of 97 percent. Such a stream also contains small amounts of acid-soluble oils and light paraffins. One proposed method for measuring the HF concentration in such a stream involves measuring the electrical conductivity of the stream. However, the electrical conductivity of a typical acid-water mixture increases as the percent of acid increases up to a maximum value and then decreases. In streams containing a substantial concentration of acid, the electrical conductivity decreases toward zero as the acid concentration approaches 100 percent. Accordingly, a simple measurement of conductivity does not provide a signal wherein the conductivity increases linearly with respect to acid concentration. Such a signal is particularly desirable in plane operations where an operator may take corrective action if there is a change in acid concentration or where an automatic control system may be actuated by such a signal.

In accordance with one aspect of this invention, a method is provided for measuring the acid concentration of a test material by diluting the test material so that the acid concentration is quite low. A measurement is then made of the electrical conductivity of the resulting mixture to provide a signal wherein the conductivity is substantially a linear function of the acid concentration. This is accomplished by adding a predetermined quantity of the sample to a stream of water which is introduced into a mixing device at a predetermined rate. The electrical conductivity of the resulting mixture is measured.

In another aspect of this invention, apparatus is provided which is particularly useful in carrying out the foregoing method. This apparatus employs a sample valve to introduce a predetermined volume of the test material into the flow path of a water stream. The effluent from the sample valve is passed through a mixing device to a conductivity detector.

In the accompanying drawing.

Figure 1:
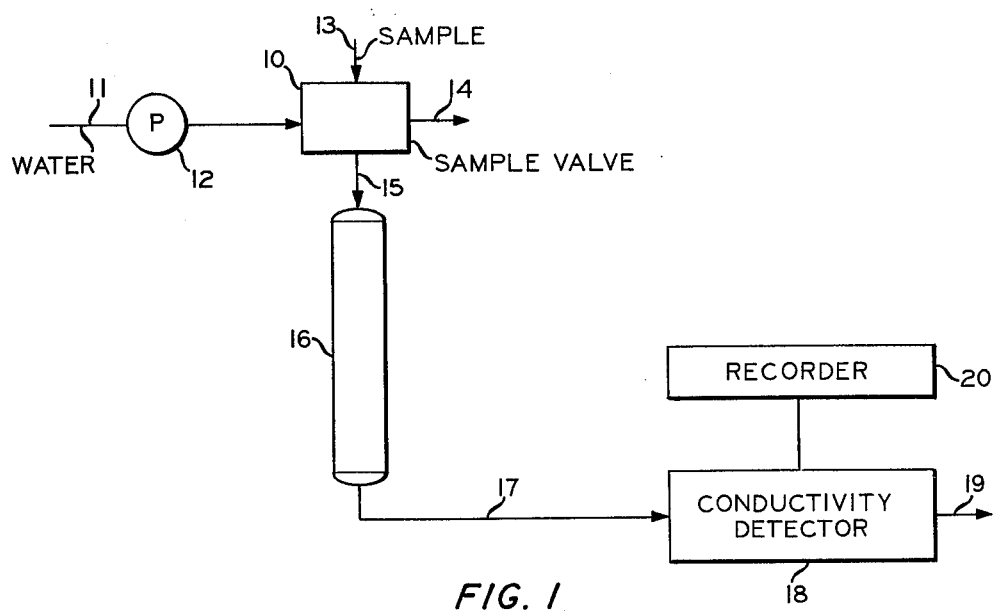
FIG. 1 is a schematic representation of apparatus constructed in accordance with this invention.

Referring now to the drawing in detail and to FIG. 1 in particular, a stream of water is introduced into a sample valve 10 through a conduit 11 which has a pump 12 therein. Pump 12 is selected to provide a constant flow of water through conduit 11. A sample stream to be analyzed is introduced into valve 10 through a conduit 13, and sample effluent is withdrawn from valve 10 through a conduit 14. A stream to be analyzed is withdrawn from valve 10 through a conduit 15 which communicates with the inlet of a mixing device 16. The effluent from device 16 is conveyed through a conduit 17 to an electrical conductivity measuring instrument 18. The effluent from this conductivity detector is removed through a conduit 19. The output signal from detector 18 is transmitted to a recorder 20.

Figure 2:
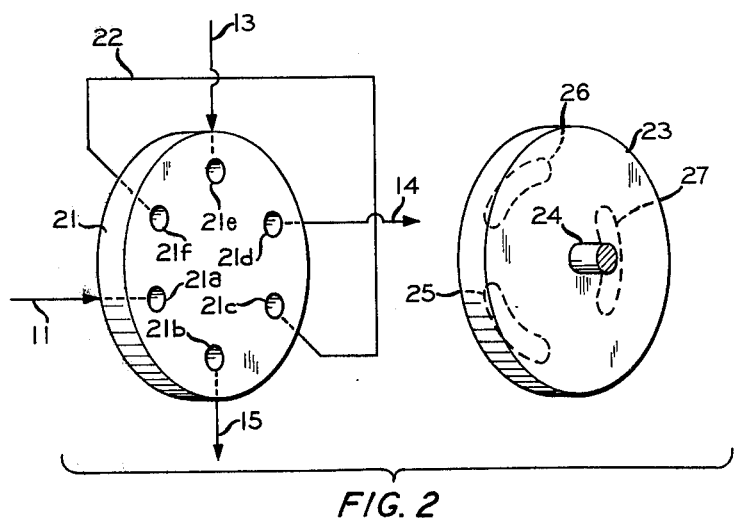
FIG. 2 is a schematic representation of an embodiment of the sample valve of FIG. 1.

Sample valve 10 can advantageously be of a type conventionally employed in chromatographic analyzers to introduce a predetermined volume of sample into a carrier stream. One such valve is illustrated schematically in FIG. 2. This valve comprises a first plate 21 which is provided with six ports 21a to 21f on the inner face thereof. Conduits 11, 13, 14 and 15 communicate with respective ports 21a, 21e, 21d and 21b. A conduit 22 communicates between ports 21c and 21f. The valve of FIG. 2 is provided with a second plate 23 which is rotatable with respect to plate 21 and which is normally positioned such that the inner surface thereof is in engagement with the inner surface of plate 21. Plate 23 can be rotated by a shaft 24. The inner surface of plate 23 is provided with three recesses 25, 26 and 27. When the plates are in engagement and occupy a first position relative to one another, ports 21a and 21b are in communication through recess 25, ports 21c and 21d are in communication through recess 27, and ports 21e and 21f are in communication through recess 26. When plate 23 is rotated to a second position, ports 21a and 21f are in communication through recess 25, ports 21d and 21e are in communication through recess 26, and ports 21b and 21c are in communication through recess 27.

Figure 3:
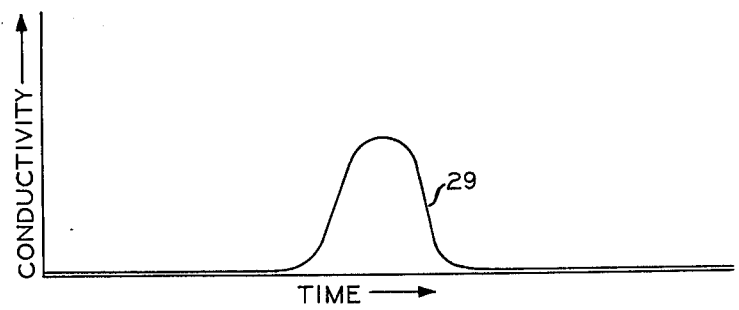
FIG. 3 illustrates a typical signal applied to the recorder of FIG. 1.

When valve 10 is in the first described position, water introduced through conduit 11 flows directly through valve 10 and mixing device 16 to detector 18. The sample stream to be analyzed flows from conduit 13 through conduit 22 and is removed through conduit 14. At this initial position, detector 18 measures the electrical conductivity of the water stream, which is substantially zero, assuming that the water does not have conducting minerals therein. The flow of sample through conduit 22 results in this conduit being filled with the sample material. When it is desired to make an analysis, the valve is moved to the second position so that the water stream from conduit 11 flows through conduit 22 before being removed through conduit 15. The sample from conduit 13 is vented through conduit 14 at this time. The flow of water through conduit 22 serves to displace the volume of sample trapped in conduit 22 and to pass this trapped volume into mixing device 16. Mixing device 16 can advantageously be a relatively small conduit packed with particulate material. The resulting mixture which is introduced into detector 18 thus constitutes a diluted sample of the test material. A typical output signal from detector 18 is illustrated in FIG. 3 where the measured electrical conductivity is plotted as a function of time. The peak height of signal 29 serves to provide a measurement of the acid concentration of the sample mixture. The apparatus can be calibrated by employing a series of samples of known acid concentrations and observing the corresponding peak heights of signals 29. In plant operations it is often desirable to make repetitive analyses. This can be accomplished by means of a timer which actuates valve 14 at predetermined time intervals. Recorder 20 can be a peak height recorder which is advanced by the timer so as to record a series of vertical lines, each representing the acid concentration of a sample.

Valve 10 and the equipment downstream thereof should be constructed of materials which are acid-resistant. Polymeric materials such as poly(tetrafluoroethylene) can be employed to advantage for this purpose. In addition to the rotary valve illustrated in FIG. 2, diaphragm operated valves such as described in U.S.

Pat. No. 3,387,496 can be employed. Detector 18 can be any instrument capable of measuring the electrical conductivity of a test liquid of the type described. One such detector is the "Conductomonitor", sold by Laboratory Data Control, Box 10235, Riviera Beach, Florida.

In a typical application of this invention, sample stream 13 can have a composition of approximately 90 percent HF, 3 percent water, 4 percent acid-soluble oils and 3 percent light paraffins. Such a mixture is typical of the recycle acid feed stream to an HF alkylation unit. In analyzing such a stream it is desirable to add a water-miscible solvent to the water stream 11 in order to dissolve the hydrocarbons present in the sample. Suitable materials for this purpose include tetrahydrofuran, isopropyl alcohol and dioxane, for example. A typical water stream introduced through conduit 11 can comprise approximately 50 percent water and 50 percent tetrahydrofuran. The water stream preferably should be substantially free of minerals, or at least have a constant mineral content. The water-tetrahydrofuran stream can be introduced at a rate of about ½ cubic centimeter per minute. Mixing device 16 can comprise a 3-foot (0.91 meter) column having an internal diameter of about ⅛ inch (0.32 cm.). Such a column can be packed with particles of polytetrafluoroethylene. Conduit 22 can be selected so that a sample of about 3 microliters is introduced into the water stream when valve 10 is actuated. This results in the acid being diluted at a ratio of approximately 100 to 1. The ratio should be selected so that the change in conductivity with change in acid concentration is substantially linear. It is desirable to maintain the apparatus of FIG. 1 in a temperature controlled oven in order to avoid temperature fluctuations. An operating temperature of about 80° F. (26.7° C.) can be employed to advantage. In another example of this invention using the same apparatus, the stream introduced through conduit 11 can comprise approximately 50 percent isopropyl alcohol and 50 percent water. Mixing device 16 can comprise a 1/16-inch (0.16 cm.) outside diameter tubing having a length of 11 feet (3.35 meters). No packing material is employed. The water and isopropyl alcohol mixture is introduced at a rate of about 0.6 milliliter per minute.

While this invention has been described in conjunction with presently preferred embodiments, it should be evident that it is not limited thereto.

What is claimed is:

1. The method of measuring the concentration of hydrofluoric acid in a test material which contains hydrofluoric acid, acid-soluble oils and light paraffins, which method comprises passing through a mixing device at a predetermined rate a first stream of water containing a water-miscible solvent capable of dissolving the hydrocarbons present in the test material, introducing a predetermined volume of said test material into said first stream upstream from said mixing device, and measuring the electrical conductivity of the resulting mixed effluent stream from said mixing device.

2. The method of claim 1 wherein the amount of said test material added to said first stream is such that said hydrofluoric acid is present in said effluent stream in a concentration range wherein the electrical conductivity of said effluent stream is substantially a linear function of the acid concentration therein.

3. The method of claim 1 wherein said solvent is tetrahydrofuran.

4. The method of claim 3 wherein said first stream comprises approximately 50 percent water and 50 percent tetrahydrofuran.

5. The method of claim 1 wherein said solvent is isopropyl alcohol.

6. The method of claim 5 wherein said first stream comprises approximately 50 percent water and 50 percent isopropyl alcohol.

* * * * *